United States Patent [19]

Coan

[11] Patent Number: 4,951,671
[45] Date of Patent: Aug. 28, 1990

[54] TONOMETRY APPARATUS

[76] Inventor: William M. Coan, 39 Southfield Cir., Concord, Mass. 01742

[21] Appl. No.: 235,347

[22] Filed: Aug. 23, 1988

[51] Int. Cl.⁵ ............................................. A61B 3/16
[52] U.S. Cl. ................................... 128/652; 128/645; 128/774; 73/79
[58] Field of Search ............... 128/645, 646, 721, 782, 128/647–652; 73/862, 382, 862.4

[56] References Cited

U.S. PATENT DOCUMENTS

| | | | |
|---|---|---|---|
| 3,150,521 | 9/1964 | MacKay et al. | 128/645 |
| 3,557,611 | 1/1971 | Adise | 128/645 |
| 3,628,526 | 4/1972 | Bigliano | 128/645 |
| 3,677,074 | 7/1972 | Murr | 128/645 |
| 3,782,188 | 1/1974 | Korber et al. | 73/862 |
| 3,934,462 | 1/1976 | Rende | 128/652 |
| 3,992,926 | 11/1976 | Berryhill | 128/652 |
| 4,192,317 | 3/1980 | Munnerlyn et al. | 128/646 |
| 4,364,399 | 12/1982 | Dashefsky | 128/774 |
| 4,729,378 | 3/1988 | Trittenbass | 128/645 |

FOREIGN PATENT DOCUMENTS 3705373  8/1987  Fed. Rep. of Germany .
 292940 11/1987  German Democratic Rep. .

Primary Examiner—Max Hindenburg
Assistant Examiner—Robin R. Longo
Attorney, Agent, or Firm—Choate, Hall & Stewart

[57] ABSTRACT

Apparatus for measuring pressure within an eye, includes an air chamber having a deformable wall portion, the air chamber being operatively coupled to a pressure sensor for measuring the pressure within the air chamber, a member interposable between a surface of the eye and the deformable wall portion, the member having a rear end arranged and adapted to inwardly deform the deformable wall portion and a front end arranged and adapted to inwardly deform the eye surface when the member is interposed between the eye surface and the deformable wall surface and the air chamber is moved relative to the eye surface in a direction that shortens the distance between the eye and the air chamber. Also, apparatus for measuring the pressure within an eye, includes a member having a front end arranged and adapted to deform the eye surface when the member is pressed inward upon the eye surface, a force sensor arranged and adapted to measure the force required for the front end to deform the eye surface to a specified degree, and an alignment sensor including a plurality of contacts affixed to the member and an element adapted and arranged to form electrical contact with one of the contacts when the member is aligned with the eye surface and the eye surface has been deformed to the specified degree.

20 Claims, 3 Drawing Sheets

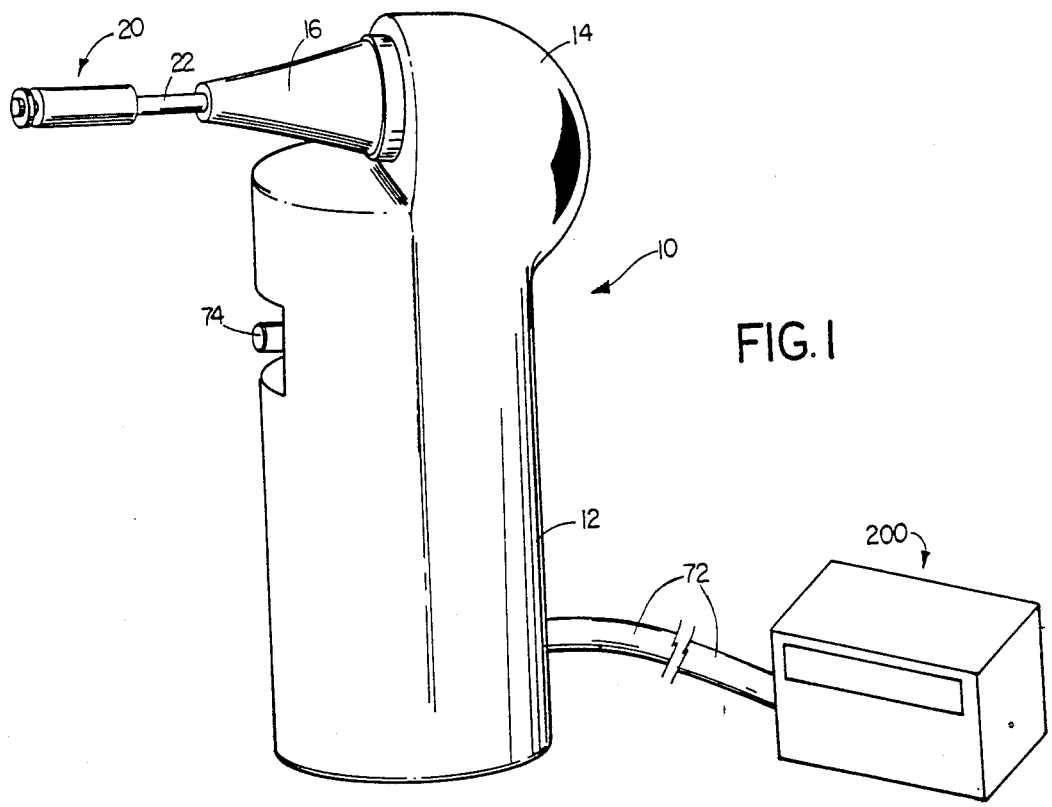
FIG. 1
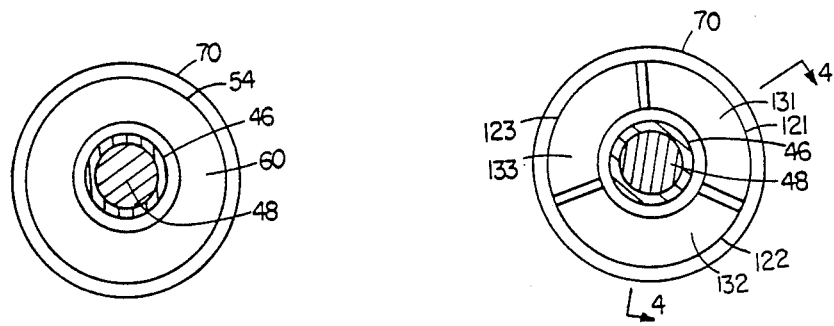
FIG. 8
FIG. 7

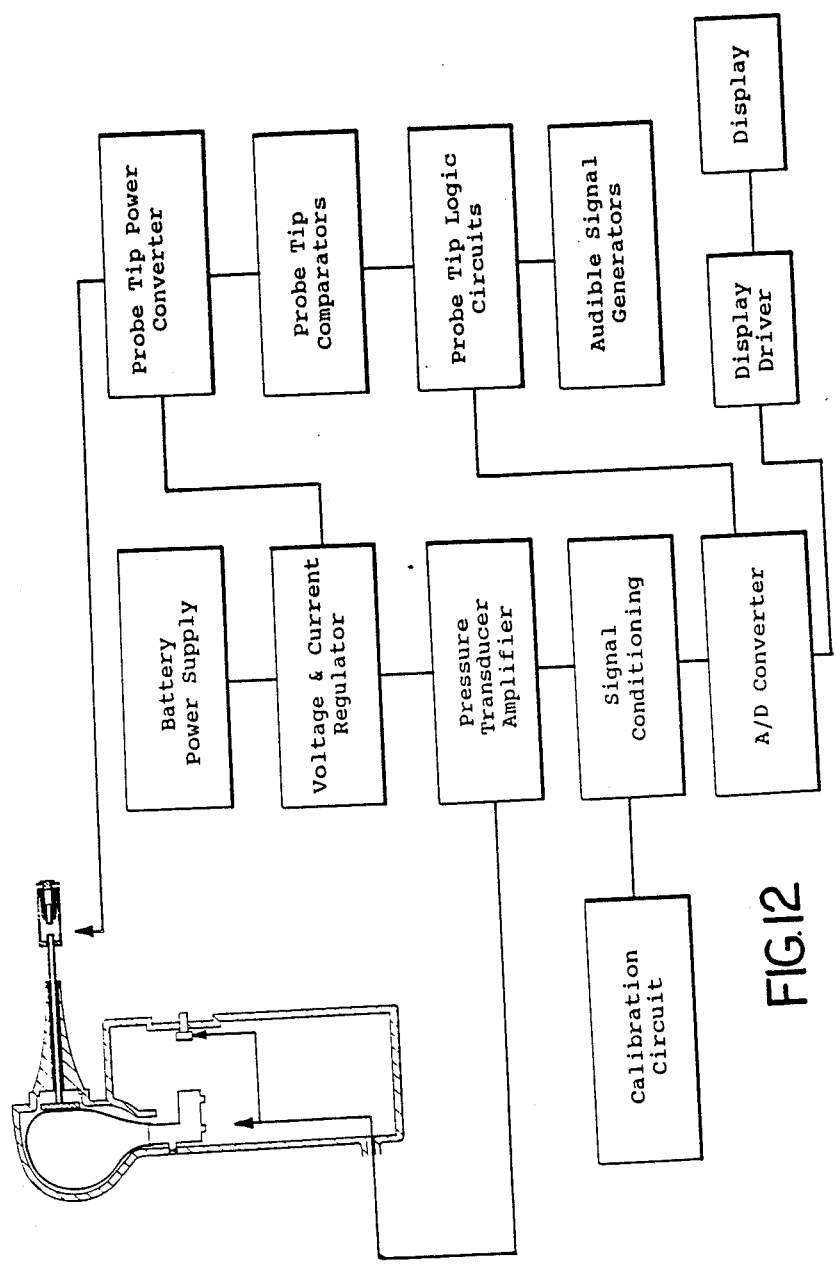

TONOMETRY APPARATUS

BACKGROUND OF THE INVENTION

This invention relates to measuring intraocular pressure.

Nearly one percent of the total population of the United States suffers from a form of blindness known as Glaucoma. Glaucoma is characterized by an increase in pressure within the eye, which causes visual defects and ultimately may cause irreversible blindness. As the intraocular pressure rises to abnormal levels, damage is caused to the ocular nerve and surrounding retinal tissues. The patient seldom experiences any symptoms that might indicate that the disease exists until major damage occurs. Typically, the patient's intraocular pressure is elevated, the retinal field is seriously diminished, ocular nerve damage occurs and there may be some degree of pain.

As part of many standard eye examinations, a test of intraocular pressure (tonometry) is performed to detect the early stages of glaucoma.

A measure of the pressure within the eye is conventionally obtained by indenting to a given depth or flattening to a given extent a portion of a measurement surface of the eye, usually the cornea, and then determining the amount of force required to produce the given flattening or indentation. The flattening or indentation is resisted by the resiliency of the measurement surface and by the internal pressure of the eyeball. The determined force is then converted to a measurement of intraocular pressure.

Commonly, the flattening or indentation is produced by contacting the tip of an instrument directly onto the measurement surface, and then pressing the tip, whose dimensions are known, against the surface toward the eye. For such measurements to be accurate, the tip of the instrument must be properly oriented with respect to the measurement surface, and the directon of pressing toward the eye must be substantially normal to the measurement surface.

Measurement of intraocular pressure using conventional apparatus generally requires that the operator subjectively judge the depth, approach angle, and position of the measuring instrument upon the eye. Operation of such devices depends upon operator skill and consistency. Operator error and the combination of these subjective variables can result in variability in measurements taken by a particular operator from time to time, as well as inconsistency in measurements taken by different operators.

Many tonometers in use employ optical systems that allow the clinician to monitor the amount of applanation or indentation of the eye to adjust the proper angle and depth of penetration. Such devices typically include a lens that rests directly upon the eye, through which the operator views the tear meniscus to judge the correctness of the applanation at the time of measurement. Such devices typically require equipment for holding the patient's head in a particular position for a time, and often employ slit lamp equipment to aid in alignment. Some time is required to set up such apparatus preparatory to each measurement.

It is generally accepted that, when properly and skillfully used, direct contact tonometers can give more valid indications of intraocular pressure, and can provide more reliable diagnosis of early stages of glaucoma, than can other types of tonometers.

A variety of disease pathogens can be found on the surface of the eye, and particularly in the fluid film that covers the eye. These include, for example, pathogens causing herpes and, possibly, acquired immune deficiency syndrome (AIDS). A disadvantage of conventional direct contact tonometers is that because they must touch the eye, they can transmit such diseases from eye to eye and patient to patient.

It has been suggested that direct contact tonometers be provided with disposable prophylactic covers, for preventing transmission of disease pathogens from one eye to another. Many known tonometers, including those which the operator aligns by employing a lens in contact with the measurement surface, cannot be modified to accommodate such covers. Those devices that have been so modified are, at least partly as a result, not sufficiently sensitive to provide accurate measurements, and they have not been accepted by the medical community as clinically practical measurement devices.

Damage to the eye sometimes occurs, owing to individual tissue susceptibility to injury, to mishap, or to operator error.

Apart from error due to subjective judgments and error of the operator, measurement error often is an effect of the design of the particular device, and especially of the particular transduction scheme.

In early tonometers, lever systems were actuated by metallic springs or cams to provide a mechanical analog of the intraocular pressure. The precision of such devices depends upon the characteristics of compressibility of the spring systems and individual units produce differing measurements to the extent that their spring systems differ. Spring fatigue and changes in temperature can cause changes in measurement.

In other known other devices strain gauges are directly coupled to the measurement surface through a metal shaft that directly contacts the eye. These, too are affected by variations in temperature, and they can be plagued with signal conditioning problems and poor schemes for calibrating the strain gauge Bridges. Some such systems cannot be calibrated by the user and consistency in manufacture or materials cannot be assured in the commercial production of such instruments.

In other known tonometers a piezoelectric crystal transducer is directly coupled to a metallic plunger which directly contacts the eye. Piezoelectric crystals can be affected by small and practically undetectable changes in temperature. Because piezoelectric transducers respond not only to force but also to temperature, varying temperatures in ambient air as well as body heat transferred throuqh the shaft from the patient to the piezoelectric crystal can interfere with precise measurement of the intraocular pressure. Moreover, the piezoelectric crystal transducer can be affected not only by temperature but also by the velocity with which the force applied to the measurement surface changes. Such devices can yield a voltage analog signal that combines contributions of the applied force, the velocity at which force is increased, and the temperature of the test environment. Further, such devices typically require use of a microprocessor for calibration and for adjustment for the non-linearity of the transducer mechanism. The user cannot easily recalibrate the device in the field.

In devices known as "non-contact" or "airpuff" tonometers, compressed gases are directed at the cornea to flatten or indent it. These are referred to as "non-contact" devices because apart from one or more bursts of air fired or released toward the eye from a predetermined distance they do not come into contact with the measurement surface. Typically in such devices an incident light wave is transmitted by light emitting diodes to the cornea, which reflects it back to phototransducers within the device. As the measured pressure of the compressed gas jet is directed toward the measurement area, the surface is flattened and a measure of reflected light yields a relative measurement of intraocular pressure. Such devices are generally considered cumbersome to operate, and obtaining consistent measurements depends upon the skill and technique of the operator in aligning the instrument at the proper distance and orientation to the eye. They are generally regarded by health care workers as useful initial screening devices, but they are not generally accepted as providing accurate measurements. The major attribute of their acceptance has been the isolation of the patient from the device to inhibit disease transmission The patient often complains of the pain associated with the blast of air that must be delivered to the eye to obtain a measurement, and many patients are often reluctant to be measured a second time by such devices.

SUMMARY OF THE INVENTION

In general, in one aspect, the invention features apparatus for measuring pressure within an eye, including an air chamber having a deformable wall portion, the air chamber being operatively coupled to a pressure sensor for measuring the pressure within the air chamber, a member interposable between a surface of the eye and the deformable wall portion, the member having a rear end arranqed and adapted to inwardly deform the deformable wall portion and a front end arranged and adapted to inwardly deform the eye surface when the member is interposed between the eye surface and the deformable wall surface and the air chamber is moved relative to the eye surface in a direction that shortens the distance between the eye and the air chamber.

In preferred embodiments the air chamber comprises a bladder, preferably made of latex; the air chamber is supported by a housing; the member is frontwardly and rearwardly moveable with respect to the housing; the member includes a shaft coupled in slidable relation to the housing; the pressure sensor includes a pressure transducer; the apparatus further includes means responsive to the pressure sensor for displaying a measure of the pressure; the apparatus further includes means responsive to the pressure sensor for recording the measure; the apparatus further includes a valve which when open provides communication between the air chamber and atmospheric air; the apparatus further includes means for aligning the member with the eye surface during the measuring; the apparatus further includes a prophylactic membrane interposed between the front end of the member and the eye surface.

In another aspect, the invention features apparatus for measuring the pressure within an eye, including a member having a front end arranqed and adapted to deform the eye surface when the member is pressed inward upon the eye surface, a force sensor arranged and adapted to measure the force required for the front end to deform the eye surface to a specified degree, and an alignment sensor including a plurality of contacts affixed to the member and an element adapted and arranqed to form electrical contact with one of the contacts when the member is aligned with the eye surface and the eye surface has been deformed to the specified degree.

In preferred embodiments said element is adapted and arranged to form electrical contact with two of the contacts when the member is aligned with the eye surface and the eye surface has been deformed to the specified degree; said sensor includes three of the contacts and the element is adapted and arranged to form electrical contact with three of the contacts when the member is aligned with the eye surface and the eye surface has been deformed to the specified degree; the element includes an element moveably affixed to the member, the element resiliently moveable forwardly and rearwardly in relation to the member; the element includes an annular piece; the contacts are sector shaped and each of the contacts has a contact surface arranged in a plane perpendicular to a frontward-rearward axis of the member; the apparatus further includes means for resiliently urging the element frontwardly; the urging means includes a spring; the spring includes a helical compression spring; the urging means includes an elastic membrane.

The tonometer of the invention can be used to accurately measure intraocular pressure throuqh a disposable prophylactic sheath, or prophylactic membrane.

The prophylactic sheath can be disposed of after each measurement and replaced before the next measurement, thus helping to prevent transmission from eye to eye and from patient to patient of pathogens that may be present on the surface of the eye. Moreover, the prophylactic sheath helps to ensure that the soft tissues of the cornea or the sclera, which are contacted during measurement, are not scratched or otherwise damaged by the instrument. Use of the prophylactic sheath does not interfere with operation of the device or with precision or accuracy of measurement.

The sheath is smooth and non-irritating, and it helps to protect the eye from direct injury that might result from operator error or inadvertent movement of the eye during contact.

The apparatus can be used by persons having no special training or experience, and provides accurate reproducible measurements objectively without respect to the level of skill of the operator.

The apparatus coordinates an alignment sensing system with a pressure measurement system so that a pressure measurement is held and displayed automatically at the moment that specified alignment and indentation criteria are met. The apparatus then notifies the operator that the alignment criteria have been met and that a measurement has been held and displayed.

The precision of measurement is not affected by temperature deviations or by changes in atmospheric pressure.

The tonometer of the invention can be employed with the patient in either a supine or sitting position, with an error in precision between measurements in the two positions of less than 1 mm Hg. Thus the invention provides for measurement of intraocular pressure during ophthalmologic surgery, with the patient in any of a variety of positions, or for ocular examination of patients who cannot be elevated, as well as during customary routine examinations, with the patients seated.

The device employs a gas pressure coupling which exerts equal pressure upon all legs of the transducer equally. The device is not affected substantially by changes in ambient temperature, or by the body temperature of the patient. Pressure equalization permits measurements to be made independently of atmospheric pressure.

The device can be battery powered for improved portability and convenience in use, and to avoid danger of electric shock to the patient. It can be used with extremely low power digital and analog technology to preserve battery power.

DESCRIPTION OF PREFERRED EMBODIMENTS

Brief Description of drawings

FIG. 1 is a perspective view of tonometer apparatus of the invention.

Fig. 7 is a somewhat diagrammatic sectional view throuqh 7—7 of the apparatus in FIG. 4.

FIG. 8 is a somewhat diagrammatic sectional view throuqh 8—8 of the apparatus in Fig. 5.

FIG. 12 is a block diagram of an electrical circuit of the apparatus.

STRUCTURE AND OPERATION

Figure 3:
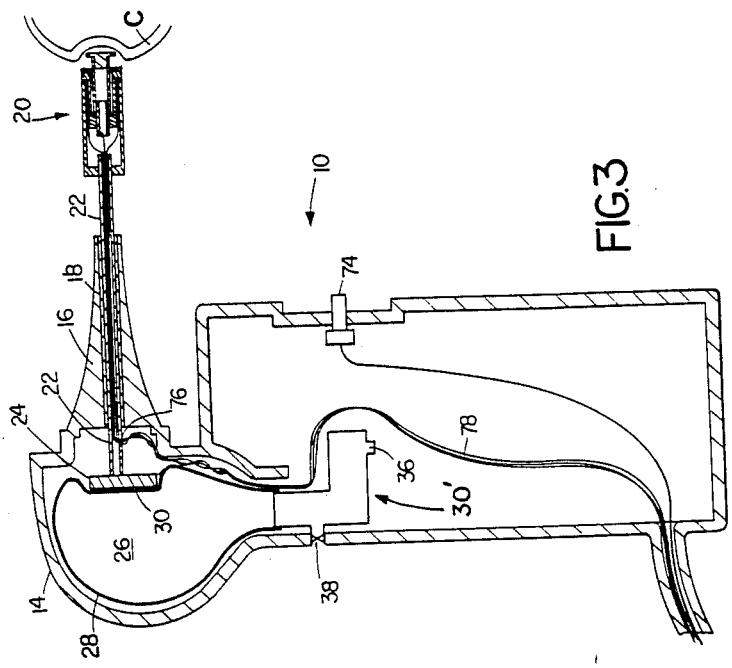
FIG. 3 is a partial view as in FIG. 2, showing the apparatus in use during a measurement.

FIG. 1 shows tonometer apparatus of the invention in a perspective view. A housing, shown generally at 10, includes handle portion 12, and head portion 14, from which nose portion 16 projects. A probe tip assembly, shown generally at 20, is affixed to the front end of shaft 22, and shaft 22 is slidably enqaqed in nose portion 16 of housing 10. A display shown generally at 200, is connected to housing 10 via cable 72. Cable 72 contains wires (not shown in FIG. 1) which provide for electrical connection between parts of display 100 and parts of housing 10 and parts of probe tip assembly 20, as further described below with reference to FIGS. 2 through 8 and 12. Reset switch 74 is provided in handle 12 for resetting the apparatus between readings, as described below.

With reference now to Fiq. 2, disk-shaped plunqer 24 is affixed to the rear end of shaft 22. Nose 16 is provided with bushing 18 to serve as a low-friction bearing surface for frontward and rearward sliding movement of shaft 22. Shaft 22 is a riqid tube. Electrically conductinq wires 78 pass through the lumen of shaft 22 from probe tip assembly 20, as shown below with reference to FIGS. 4 through 11. Wires 78 pass by way of hole 76 out of the lumen of shaft 22 and into housing 10. Housing head portion 14 contains air chamber 26, enclosed by a chamber wall 28 having the form of a bladder. When probe tip 20 is moved rearward with respect to housing 10, shaft 22 brings the rear surface of plunqer 24 in contact with the front surface of a deformable front portion 30 of wall 28. Continued rearward movement of probe tip 20 causes plunger 24 to rearwardly displace deformable front wall portion 30, as shown in FIG. 3.

Figure 2:
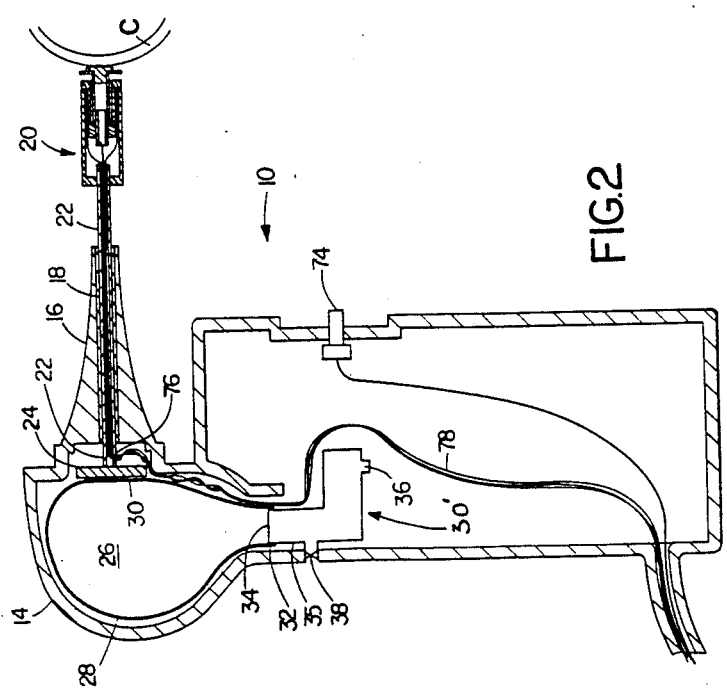
FIG. 2 is a somewhat diagrammatic sectional view of the apparatus of FIG. 1, made through the axis of the probe tip assembly, showing the apparatus ready for taking a measurement.

With reference now to FIGS. 2 and 3, handle portion 12 contains a pressure transducer, shown schematically generally at 30', which communicates with air chamber 26 by way of air chamber port 34. Elastic mouth 32 of wall 28 enclosing air chamber 26 is stretched over flange 35 extending from air chamber port 34 to couple wall 28 with transducer 30' in sealed relation. Pressure transducer 30' is provided with differential intake port 36, which communicates with ambient air, and with pressure equalizer valve 38, by which air can be taken into or exhausted from chamber 26. When pressure equalizer valve 38 is closed, as will be appreciated by one skilled in the art of pressure measurement, pressure transducer 30' in effect compares the pressure within air chamber 26 via air chamber port 34 with ambient atmospheric pressure via differential intake port 36. When pressure equalizer valve 38 is open to the atmosphere, the two pressures are equal. Rearward displacement of deformable wall portion 30 decreases the volume of air chamber 26; when air chamber valve 38 is open, such a volume decrease results in exhausting a portion of the air out from air chamber 26 through air chamber valve 38. On the other hand, when pressure equalizer valve 38 is closed, rearward displacement of deformable wall portion 30 compresses the air contained within air chamber 26 and increases the pressure sensed by the pressure transducer via air chamber port 34.

Housing 10 is preferably molded of a sturdy plastic. Wall 28 of air chamber 26 is preferably a bladder made of latex.

Pressure transducer 30' is preferably of the gage pressure type, such as, for example, the one of the SCX Series transducers, available commercially from Sen-Sym, 1255 Reamwood Avenue, Sunnyvale, CA 94089.

Correct alignment of the probe with the surface of the eyeball at the time of measurement is ensured by means of the probe tip assembly 20, as illustrated in FIGS. 4 through 8. Probe tip body 40, having a generally cylindrical shape, is affixed near the front end of shaft 22. A tubular support piece 42, made of an electrically-conductinq material, is affixed to a rearwardly recessed portion 44 of probe tip body 40. Shaft 22, support piece 42, and cylindrical probe tip body 40 are all generally axially aligned. Bushing 46, also of an electrically-conducting material, is pressed rearwardly over a frontwardly-projecting portion of support piece 42 so that the inner surface of bushing 46 makes electrical contact with the outer surface of the frontwardly-projecting portion of support piece 42. Compression coil spring 52 is placed over bushing 46, and annular conductor 54 is placed over bushing 46 so that a portion of rear surface 60 of conductor 54 rests against and makes electrical contact with a forward coil of spring 52. A cylindrical portion 48 of cap 46 is press-fitted into the front end of support piece 42 until stopped by disc-shaped probe tip portion 50 of cap 46. Spring 52 resiliently urges conductor 54 frontward with respect to probe tip body 40, permitting conductor 54 to move rearward in generally coaxial relation to support 46 when force is applied to conductor 54 in a generally rearward direction. Coil spring 52 also contacts the outer surface of support piece 46. Electrically conducting wire 100, which is one of four wires 78 passing within the lumen of shaft 22, is electrically connected to support piece 46, as indicated at 110. Electrical continuity is thus established between wire 100 and annular conductor 54 throughout the range of frontward and rearward motion of conductor 54.

Figure 4:
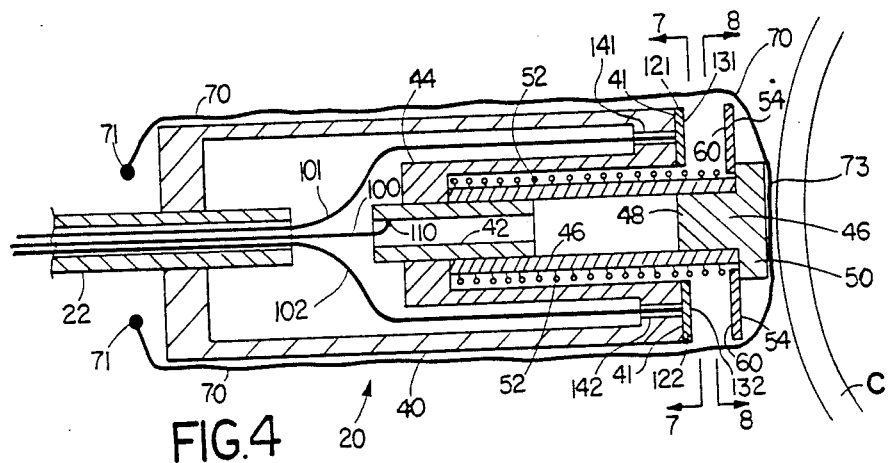
FIG 4 is a somewhat diagrammatic sectional view as in Fig. 2, showing the probe tip assembly ready for taking a measurement.
Figure 5:
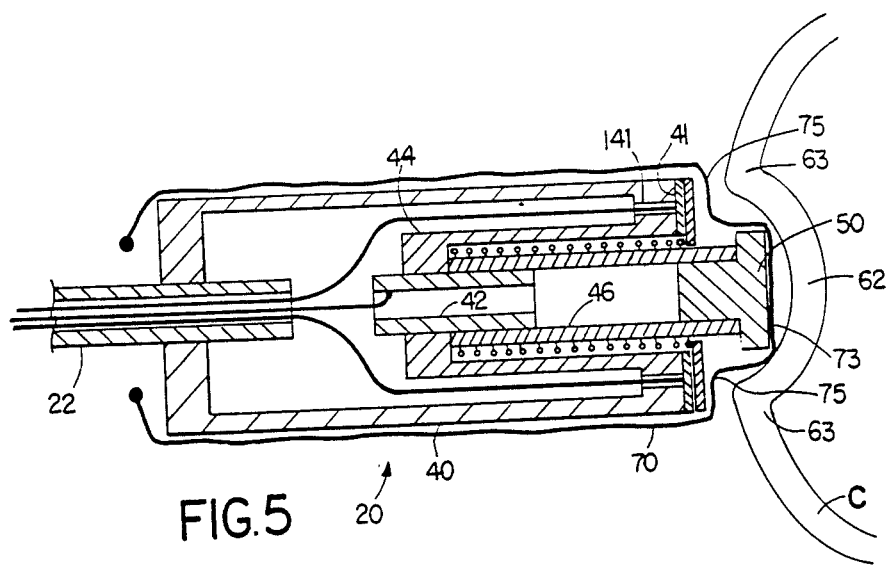
Fig. 5 is a somewhat diagrammatic sectional view as in FIG. 3, showing the probe tip assembly properly aligned with the eyeball surface during a measurement.
Figure 6:
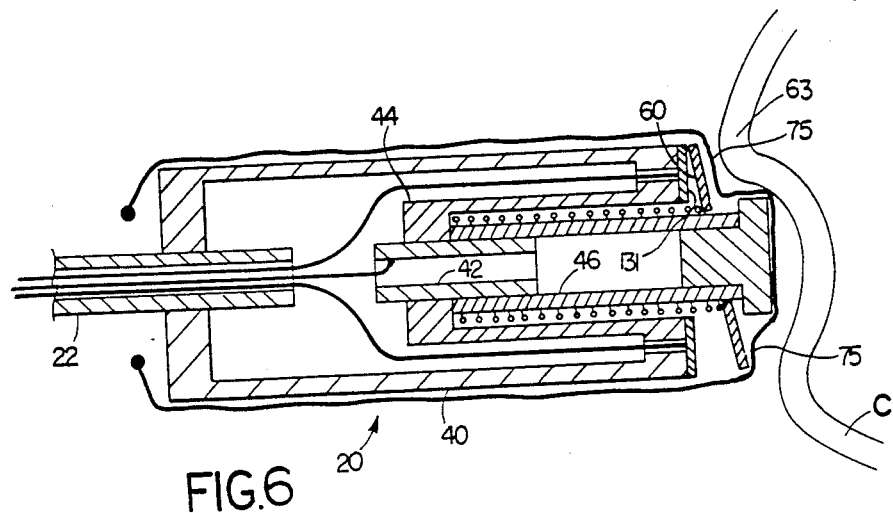
Fig. 6 is a somewhat diagrammatic sectional view as in Fig. 5, showing the probe tip assembly misaligned with the eyeball surface during an attempt to take a measurement.

Affixed to annular front surface 41 of probe tip body 40 are sector-shaped electrical contacts 121, 122, 123, of which only 121 and 122 are shown in Fig. 4 through 6, which have anterior surface 131, 132, 133, respectively, as shown more clearly in Fiq. 7. Contacts 121, 122, 123 are electrically connected respectively to electrically conducting wires 101, 102, 103, of which only 101 and 102 are shown in FIGS. 4 through 6. Wires 101, 102, 103 pass through the lumen of shaft 22 and through holes 141, 142, 143, respectively, of which only 141 and 142 are shown in FIGS. 4 through 6, in the anterior wall of probe tip body 40. Latex sheath 70 is drawn over and encloses probe tip 50, annular conductor 54, and contacts 121, 122, 123 and is held in place over probe tip body 40 by elastic annular bead 71 in such fashion that it does not interfere with movement of annular conductor 54, as described below with reference to FIGS. 5 and 6. Latex sheath 70 provides a disposable prophylactic membrane which can be replaced between measurements.

As the operator, holding housing handle portion 12 in hand, begins to press probe tip assembly 20 against the cornea C of the eye, the portion of sheath 70 overlying probe tip 50 contacts the outer surface of the cornea. As the operator proceeds to move the apparatus forward probe tip 50, overlain by a central portion 73 of sheath 70, begins to deform the cornea or measurement surface. This deformation is resisted by the cornea and by the internal pressure of the eye, and shaft 22 begins to move rearward with respect to housing 10, pressing plunger 24 against deformable wall 30 of air chamber 26 as described above generally with respect to Fig. 2. As the deformation increases, an indentation forms in cornea C at the location 62 where probe tip 50 presses against central portion 73 of sheath 70. Concurrently, an edge of the indentation forms at regions 63 of cornea C situated radially away from location 62. These regions 63 press rearward against the areas 75 of sheath 70 overlying the edge of probe tip 50, and this rearward pressure causes a rearward displacement of annular conductor 54 with respect to probe tip 50, probe tip body 40, and shaft 22. As long as probe tip assembly 20 is properly aligned with the surface of the cornea, as illustrated for example in FIG. 4, the regions 63 press nearly equally rearward, and annular conductor 54 remains substantially perpendicular to the axis of the probe tip assembly as it is rearwardly displaced relative to probe tip body 40.

With reference now to Fiq. 6, when the probe tip assembly is misaligned with respect to the corneal surface as the cornea C is deformed, regions 63 press rearward against only a portion of the areas 75 overlying the edge of probe tip 50, and as a result annular conductor 54 is displaced out of perpendicular with respect to the axis of the probe tip assembly 20; as the misaligned rearward displacement of conductor 54 with respect to probe tip 50 and probe tip body 40 proceeds, eventually a portion of rear surface 60 of annular conductor 54 contacts one (or possibly two but not all) of front surfaces 131, 132, and 133 of contacts 121, 122, 123. When fewer than all of the contacts are contacted by the annular conductor, a "nonaligned" signal is produced, as described below with respect to FIG. 12.

Fig. 12 is a block diagram showing electronic circuitry for use in conjunction with the probe apparatus of FIGS. 1 through 8. Electrical power supplied by a battery power supply passes to a voltage and amperage regulator to provide a predetermined reference potential and current for the sensitive air pressure transducer bridge and amplifier circuits.

The electronic circuitry includes components that produce pressure data relating to the pressure within the air chamber, components that produce signals relating to whether or not the instrument is correctly aligned, components that inform the operator of the condition of alignment, and components recording a pressure measurement at the moment the alignment is correct and the prescribed indentation of the corneal surface has been produced, as described above and illustrated in FIGS. 5 and 10.

Figure 9:
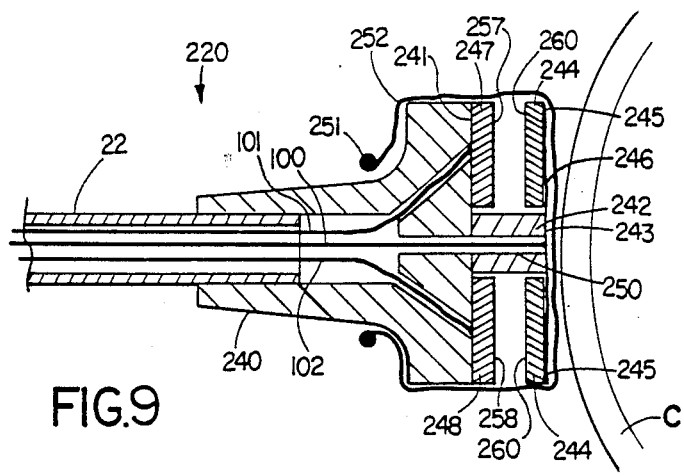
Fig. 9 is a somewhat diagrammatic sectional view as in FIG. 2, showing an alternative probe tip assembly ready for taking a measurement.
Figure 10:
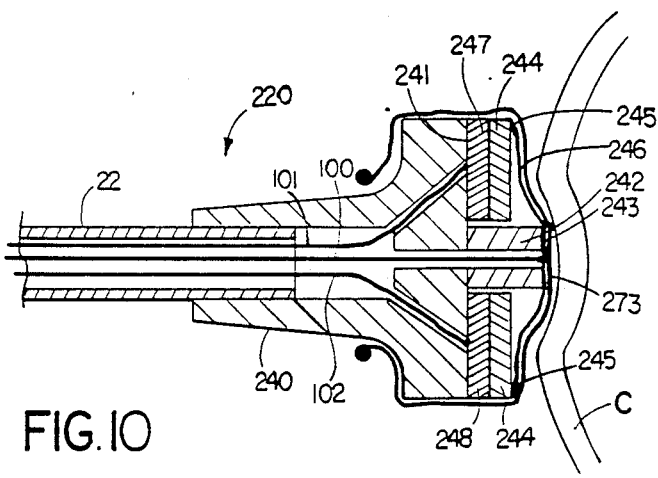
FIG. 10 is a somewhat diagrammatic sectional view as in FIG. 9, showing the alternative probe tip assembly properly aligned with the eyeball surface during a measurement.
Figure 11:
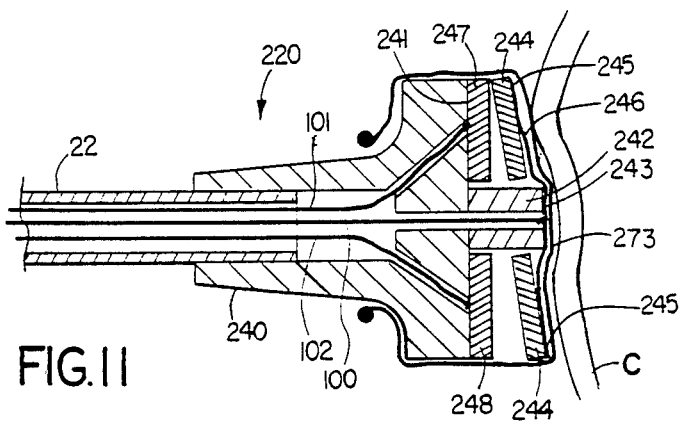
FIG. 11 is a somewhat diagrammatic sectional view as in FIG. 9, showing the alternative probe tip assembly misaligned with the eyeball surface during an attempt to take a measurement.

An alternative probe tip assembly is shown generally at 220 in FIGS. 9 through 11. Probe tip body 240 is affixed to the front end of shaft 22. Affixed to circular front surface 241 of probe tip body 240 is cylinder-shaped probe tip 242. Shaft 22, probe tip body 240, and probe tip 242 are all axially aligned. Circular elastic membrane 246 is affixed near its center to front surface 243 of probe tip 242, and the marginal portion of the front surface 245 of annular conductor 244 is affixed to the edge portion of circular elastic membrane 246. Elastic membrane 24 thereby holds annular conductor in coaxial relation to probe tip 242. Affixed to anterior surface 241 of probe tip body 240 are sector-shaped electrical contacts 247, 248 and 249, which have anterior surfaces 257, 258, and 259, respectively. Each of contacts 247, 248, and 249 is electrically connected to a signal generator by way of electrically-conductinq wires 101, 102, 103 which pass through the lumen of shaft 22 and through holes in probe tip body 240, in a manner similar to that described above with reference to FIG. 9. Elastic membrane 246 is treated for example by electrospattering so that it is electrically conductive, and it is electrically connected to a signal generator by way of electrically-conducting wire 100 which passes through the lumen of shaft 22 and throuqh hole 250 in probe tip 242.

Latex sheath 252 is drawn over and encloses electrically conducting elastic membrane 246, probe tip 242, annular conductor 244, and contacts 247, 248, and 249, and is held in place by elastic annular bead 251 in such fashion that it does not interfere with the movements of annular conductor 244. Latex sheath 252 thus provides a prophylactic membrane which can be disposed of between measurements.

This embodiment, in which the annular conductor is held in coaxial relation to probe tip 242, and is resiliently urged frontward, by means of elastic membrane 246, operates similarly to the embodiment described above with reference to FIGS. 4 throuqh 8, as will be readily apparent by reference to FIG. 9 through 11. As the operator, holding housing handle portion 12 in hand, begins to press probe tip assembly 20 against the cornea C of the eye, the portion of sheath 250 overlying probe tip 242 contacts the outer surface of the cornea As the operator proceeds to move the apparatus forward probe tip 242, overlain by a central portion 273 of sheath 246, begins to deform the cornea. Eventually portions of rear surface 260 of annular conductor 244 come into contact with surfaces 257, 258, 259 of contacts 247, 248, 249. When conductor 244 makes contact concurrently with all three contacts 247, 248, 249, as shown in FIG. 10, an "alignment" signal is generated; when fewer than all of the contacts are contacted by the annular conductor, a "nonaligned" signal is produced, as described above with respect to FIG. 12.

PRESSURE

As the cornea and the intraocular pressure force the probe tip assembly and shaft rearward with respect to the housing, pressing the plunqer against the deformable wall of the air chamber and increasing the air pressure within the chamber, as described above with reference to FIGS. 3 and 4, the pressure transducer produces an electrical analog of the pressure developed within the air chamber. The electrical analog is amplified by a pressure transducer ratiometric amplifier and referenced by a calibration circuit and a signal conditioning circuit, and the resulting potential is sent to an analog to digital (A/D) converter, which generates a digital representation of the pressure.

The digital pressure signal from the A/D converter can be either directed to a microprocessor for additional treatment, or presented directly to a display driver and then to a display transducer, such as liquid crystal display (LCD) which presents the intraocular in terms of millimeters of mercury (mm Hg).

ALIGNMENT

A regulated potential from the voltage and current regulator is reduced by a probe tip power converter and independently distributed by way of wires 101, 102, 103 to contacts 121, 122, 123 and to annular conductor 54. When the conductor makes contact one or more of the three contacts, probe tip comparators alert a probe tip logic circuits, which determine whether fewer than all the contacts have been contacted by the conductor (indicating misalignment), or whether all three contacts have been contacted by the conductor concurrently (an alignment). If the probe tip logic circuits determine that there is a misalignment, then the logic circuits instruct an audible signal generator to produce an audible signal indicating to the operator that a misalignment has occurred. If, on the other hand, the probe tip logic circuits determine that there is an alignment, then the logic circuits instruct the A/D converter to direct the digital pressure signal to the display driver and then to the (LCD) for presentation of the intraocular pressure. Moreover, if the probe tip logic circuits determine that there is an alignment, then they instruct the audible signal generator to produce an audible signal, distinguishable from the misalignment signal, indicting to the operator that an alignment has occurred, and that a signal has been sent from the A/D converter to the display driver and the display.

USE

The tonometer apparatus of the invention can be used by an operator with little training and having no special skills, generally as follows.

At the outset the operator fits a sterile sheath over the probe tip assembly, following sterile procedure as will be familiar to health care workers generally. Then, prior to taking a measurement of intraocular pressure, pressure equalization port 38 is opened to allow the air pressure within the air chamber and the pressure transducer to equalibrate to atmospheric pressure, which is sampled by the pressure transducer at differential intake port 36. Once equilibration has occurred, pressure equalization port 38 is closed. At this point the pressure within air chamber 26 equals ambient atmospheric pressure, unless or until the atmospheric pressure changes or a force upon probe tip assembly 20 causes shaft 22 to move rearward with respect to housing 10, causing plunger 24 to press against deformable wall 30 of the air chamber. This initial equilibration step removes influences of atmospheric pressure on the measurement.

Once equilibration has been completed, the operator brings the apparatus to the eye, addressing the cornea with the probe tip assembly oriented as nearly normal to the corneal surface as can be estimated. As the operator presses the apparatus forward toward the eye, so that probe tip assembly 20 of the device is gently forced against the corneal surface, the resistance exerted by the cornea and by the intraocular pressure causes plunger 24 to press against deformable wall 30, raising the pressure within air chamber 26. Transducer 30' detects and measures the difference between ambient atmospheric pressure, detected at differential intake port 36, and the intraocular pressure, as transferred to air chamber 26 through probe tip assembly 20, shaft 22, and plunger 24.

If the probe tip assembly is misaligned, for example as described above with reference to FIG. 6, the alignment circuitry will so inform the operator by an auditory signal, as described above with reference to FIG. 9, and the operator can then withdraw the probe from the eye, make a correction in alignment, and readdress the cornea with the probe tip assembly.

The operator repeats the attempts if necessary, retreating each time a misalignment signal is heard, until the alignment circuitry informs the operator, as described above with reference to FIG. 9, that the device has been pressed sufficiently far toward the eye that an indentation has been made, without misalignment, to the correct depth, as described above with reference to FIG. 5. The alignment circuitry will at that moment have instructed the pressure circuitry to hold and display the pressure within the air chamber, and the operator can take the pressure measurement from the display.

After the operator has examined the displayed measurement, the circuitry is reset by means of a reset circuit button The operator can then take additional measurements on the same eye, or can replace the contaminated sheath before making measurements on the next eye. The contaminated sheath is replaced by removing it from the probe tip assembly, and the apparatus is ready to be fitted with a sterile sheath and reequilibrated in preparation for the next measurement.

OTHER EMBODIMENTS

Other embodiments are within the following claims. For example, one or more of the various audible signals can be converted to visual display signals to notify the operator that a measurement has been taken or that the instrument is misaligned.

The probe tip can be pressed into the sclera than into the cornea. Because the sclera itself resists indentation more firmly than the corneal wall itself, a specified force against the sclera produces a shallower indentation than against the cornea of the same eye. The apparatus can readily be calibrated to accommodate this difference.

The output of the A/D converter can be presented to other forms of microprocessors or computers for additional analysis or to save test results in an electronic memory.

The device can be used without the sheath, but it is preferred that the sheath be used, because it protects the corneal tissues from injury and because it can be discarded between measurements, preventing the spread of disease.

The frontwardly and backwardly moving conductor can have a shape other than the annular shape described, provided that it forms electrical contact with the contacts when the alignment and the degree of deformation of the measurement surface of the eye is suitable. The contacts can number two, three, or more than three. The arrangement of contacts described above is preferred because it provides a highly stringent alignment criterion. That is, an alignment signal is produced only when the conductor and the contacts are coplanar, and only when the conductor has been pressed fully rearward. Other less stringent criteria can be used For example, the probe tip logic circuits can be set up to produce an alignment signal when the conductor has made electrical contact with only one, or with only two of the contacts Moreover, the probe tip logic can be set up to produce different signals depending upon which of the contacts has been electrically contacted by the conductor, to inform the operator in what direction the device should be moved to correct a misalignment.

I claim:

1. Apparatus for measuring pressure within an eye, comprising
   an air chamber supported by a housing, said air chamber having a deformable wall portion,
   a pressure sensor responsive to pressure within said air chamber for measuring the pressure within said air chamber, and
   a member interposable between a surface of the eye and said deformable wall portion, said member having a rear end and a front end, said member being substantially non-compressible along its front-to-rear direction, said member being engaged with said housing such that said member is frontwardly-and-rearwardly moveable with respect to said deformable wall portion of said air chamber, whereby when said member is interposed between the eye surface and said deformable wall surface and said housing is moved relative to the eye surface in a direction that shortens the distance between the eye and the air chamber said front end inwardly deforms the eye surface and said rear end inwardly deforms said deformable wall portion, raising the pressure within said air chamber, measured by said pressure sensor.

2. The apparatus of claim 1 wherein said air chamber comprises a bladder.

3. The apparatus of claim 1 wherein said member comprises a shaft coupled in slidable relation to said housing.

4. The apparatus of claim 1 wherein said pressure sensor comprises a pressure transducer.

5. The apparatus of claim 1 or 2 wherein said air chamber comprises latex.

6. The apparatus of claim 1, further comprising means responsive to said pressure sensor for displaying a measure of said pressure.

7. The apparatus of claim 1, further comprising means responsive to said pressure sensor for recording said measure.

8. The apparatus of claim 1, further comprising a valve which when open provides communication between said air chamber and atmospheric air.

9. The apparatus of claim 1, further comprising means for aligning said member with the eye surface during said measuring.

10. The apparatus of claim 1, further comprising a prophylactic membrane interposed between said front end of said member and the eye surface.

11. Apparatus for measuring pressure within an eye, comprising
    a member moveably engaged with a housing, having a front end for deforming the eye surface when said member is pressed inward upon the eye surface,
    a force sensor means supported by said housing, responsive to movement of said member for measuring the force required for said front end to deform the eye surface to a specified degree, and
    an alignment sensor comprising a plurality of contacts affixed to said member, and an element associated with and moveable relative to said member in response to deformation of the eye surface, whereby said element forms electrical contact with one of said contacts when said member is aligned with the eye surface and the eye surface has been deformed to the specified degree.

12. The apparatus of claim 11 wherein said element forms electrical contact with two of said contacts when said member is aligned with the eye surface and the eye surface has been deformed to said specified degree.

13. The apparatus of claim 11 wherein said element forms electrical contact with three of said contacts when said member is aligned with the eye surface and the eye surface has been deformed to said specified degree.

14. The apparatus of claim 11 wherein said element comprises an element moveably affixed to said member, whereby said element is moveable forwardly and rearwardly in relation to said member.

15. The apparatus of claim 14 wherein said element comprises an annular piece.

16. The apparatus of claim 14 wherein said contacts are sector shaped and each of said contacts has a contact surface arranged in a plane perpendicular to a frontward-rearward axis of said member.

17. The apparatus of claim 14, further including means for resiliently urging said element frontwardly.

18. The apparatus of claim 17 wherein said urging means comprises a spring.

19. The apparatus of claim 18 wherein said spring comprises a helical compression spring.

20. The apparatus of claim 17 wherein said urging means comprises an elastic membrane.

* * * * *

UNITED STATES PATENT AND TRADEMARK OFFICE
CERTIFICATE OF CORRECTION

PATENT NO. : 4,951,671

DATED : August 28, 1990

INVENTOR(S) : William M. Coan

It is certified that error appears in the above-identified patent and that said Letters Patent is hereby corrected as shown below:

```
Column 3, line 20:  after "transmission", please insert -- . --.
          line 34:  replace "arranqed" with -- arranged --.
          line 60:  replace "arranqed" with -- arranged --.
Column 5, line 33:  replace "throuqh" with -- through --.
          line 54:  replace "enqaqed" with -- engaged --.
          line 64:  replace "plunqer" with -- plunger --.
          line 68:  replace "riqid" with -- rigid -- and replace
                    "conductinq" with -- conducting --.
Column 6, line 8:   replace "plunqer" with -- plunger --.
          line 55:  replace "conductinq" with -- conducting --.
Column 7, line 19:  replace "Fiq." with -- Fig. --.
Column 8, line 37:  replace "24" with -- 246 --.
          line 43:  replace "conductinq" with -- conducting --.
          line 51:  replace "throuqh" with -- through --.
          line 65:  replace "throuqh" with -- through --.
Column 9, line 2:   after "cornea", please insert -- . --.
          line 19:  replace "plunqer" with -- plunger --.
          line 34:  after "intraocular", please insert --
                    pressure --.
Column 10, line 52: after "button", please insert -- . --.
           line 66: after "sclera", please insert -- rather --.
Column 11, line 28: after "used", please insert -- . --.
```

UNITED STATES PATENT AND TRADEMARK OFFICE
CERTIFICATE OF CORRECTION

PATENT NO. : 4,951,671

DATED : August 28, 1990

INVENTOR(S) : William M. Coan

It is certified that error appears in the above-identified patent and that said Letters Patent is hereby corrected as shown below:

Column 11, line 31: after "contacts", please insert -- . --.

Signed and Sealed this

Twenty-sixth Day of November, 1991

*Attest:*

HARRY F. MANBECK, JR.

*Attesting Officer*     *Commissioner of Patents and Trademarks*